United States Patent [19]

Scheuermann et al.

[11] 4,075,211

[45] Feb. 21, 1978

[54] NAPHTHALIMIDE COMPOUNDS AND OPTICAL BRIGHTENERS

[75] Inventors: Horst Scheuermann; Albert Hettche, both of Ludwigshafen, Germany

[73] Assignee: BASF Aktiengesellschaft, Ludwigshafen, Germany

[21] Appl. No.: 646,181

[22] Filed: Jan. 2, 1976

[30] Foreign Application Priority Data

June 20, 1973 Germany .............................. 2331307

Related U.S. Application Data

[63] Continuation-in-part of Ser. No. 479,892, June 17, 1974, abandoned.

[51] Int. Cl.$^2$ ................ C07D 221/14; C07D 401/06; C09K 11/06; C07D 413/06
[52] U.S. Cl. .......................... 260/270 H; 260/281 N; 260/281 NH; 106/288 Q; 252/301.25; 252/301.26; 544/126
[58] Field of Search ........ 260/281 N, 281 NH, 270 H

[56] References Cited

U.S. PATENT DOCUMENTS

| | | | |
|---|---|---|---|
| 3,310,564 | 3/1967 | Kasai | 260/281 |
| 3,625,947 | 12/1971 | Noguchi et al. | 260/281 |
| 3,697,525 | 10/1972 | Okada et al. | 260/281 |
| 3,804,838 | 4/1974 | Mingasson et al. | 260/281 |
| 3,849,331 | 11/1974 | Mingasson et al. | 260/281 |
| 3,935,227 | 1/1976 | Wade et al. | 260/281 |

FOREIGN PATENT DOCUMENTS

39/27127  11/1964  Japan .................................. 260/281

OTHER PUBLICATIONS

Scheuermann et al., Chem. Abs. 83, 12224c(1975).

*Primary Examiner*—Donald G. Daus
*Assistant Examiner*—Mark L. Berch
*Attorney, Agent, or Firm*—Keil, Thompson & Shurtleff

[57] ABSTRACT

Compounds of the naphthalimide series which in the dissolved condition exhibit a characteristic blue, violet or bluish violet fluorescence, and a process for their production. The compounds are outstandingly suitable for the optical brightening of synthetic fibers.

9 Claims, No Drawings

NAPHTHALIMIDE COMPOUNDS AND OPTICAL BRIGHTENERS

This application is a continuation-in-part of our co-pending application Ser. No. 479,892, filed 6/17/74, now abondoned.

The invention relates to compounds of the formula (I):

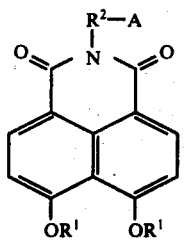

in which
R$^1$ is C$_1$- to C$_4$-alkyl or C$_1$- to C$_4$-alkoxyethyl, R$^2$ is branched C$_3$- to C$_6$-alkylene,
A is

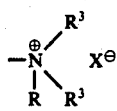

R is hydrogen, C$_1$- to C$_4$-alkyl, allyl or benzyl,

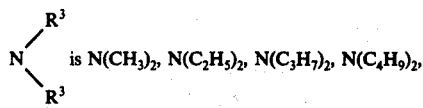 is N(CH$_3$)$_2$, N(C$_2$H$_5$)$_2$, N(C$_3$H$_7$)$_2$, N(C$_4$H$_9$)$_2$,

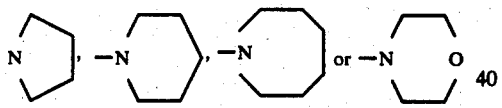

and
X$^-$ is an anion.

Preferred compounds of formula (I) are those in which:
R$^1$ is C$_1$- to C$_4$-alkyl or CH$_3$OC$_2$H$_4$.
R$^2$ is branched C$_4$-alkylene, and
A is a pyrrolidine, piperidine or hexamethyleneimine.

Examples of alkyl R$^1$ are preferably methyl, ethyl, propyl, butyl, methoxyethyl and ethoxyethyl.

Examples of linear and branched hydrocarbon radicals for R$^2$ are those characterized by the following formulae:

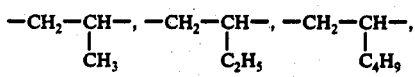

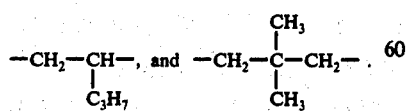

Anions X$^-$ for the ammonium compounds include the usual anions such as perchlorate, chloride, bromide, sulfate, hydrogen sulfate, methyl sulfate, ethyl sulfate, acetate, formate, benzenesulfonate, toluenesulfonate, chlorozincate and tetrafluoborate.

The compounds of the formula (I) are pale yellow substances which are suitable for the optical brightening of synthetic fibers, particularly anionically modified polyamides, polyesters and acrylonitrile polymers and copolymers and also cellulose esters such as acetate silk, particularly cellulose triacetate. The quaternary compounds, because of their very good crystallizability, may be recovered in particularly high purity and they are eminently suitable for application to acrylonitrile polymers because of their outstanding solubility in water and their excellent dyeing behavior.

In the dissolved condition, for example in water or in an organic solvent, the compounds exhibit a characteristic bluish violet or violet fluorescence. The dyeings are characterized by excellent whiteness and good lightfastness.

Compounds of formula (I) may be prepared by reaction of a 4,5-dihalonaphthalic anhydride (formula (II)) with a compound of formula (III) to form the corresponding naphthalimide (formula IV), substitution of the halogen atoms by the alkoxy —OR$^1$ and quaternization of the reaction product by an alkylating agent by a conventional method according to the following equations:

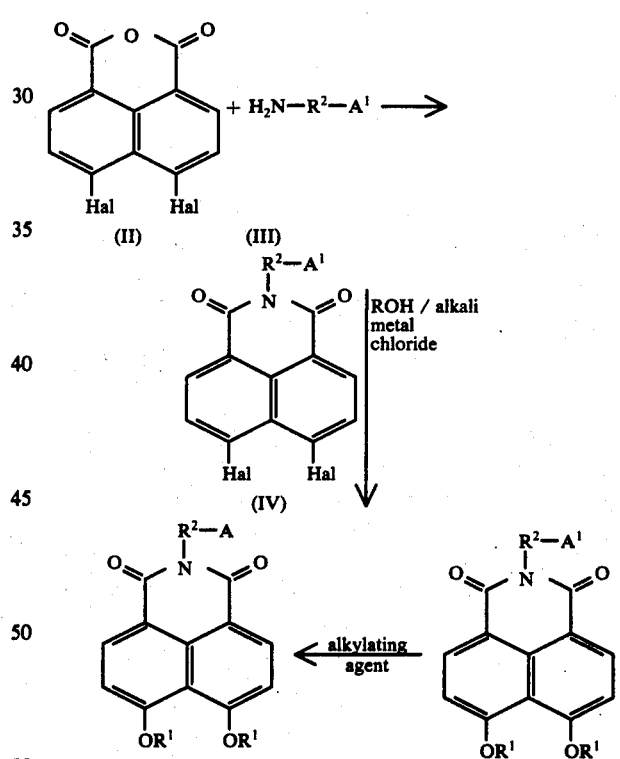

Hal may be bromine or preferably chlorine and A$^1$ is

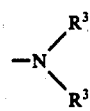

Sodium methoxide is preferred as the alkali metal alkoxide. Examples of particularly suitable alkylating agents for quaternizing the nitrogen include dimethyl sulfate, diethyl sulfate, allyl bromide, benzyl chloride and the methyl ester of p-toluenesulfonic acid.

The following Examples illustrate the invention. Parts and percentages specified are by weight.

EXAMPLE 1

136 parts of 4.5-dimethoxy-N(1-piperidino-butyl-2)-naphthalimide is dissolved in 500 parts of hot acetone. 52 parts of dimethyl sulfate is dripped in at 56° C.

After a reaction period of three hours the whole is cooled, suction filtered and washed with acetone.

176 parts of the following compound is obtained which exhibits violet fluorescence in solution in dimethylformamide.

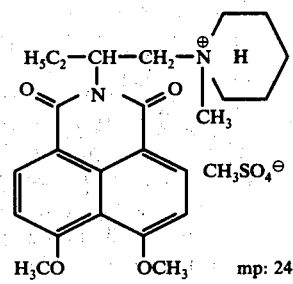

mp: 245-248° C 4.5-dimethoxy-N(1-piperidino-butyl-2)-naphthalimide is obtained by reaction of 150 parts of 4.5-dichloro-N(1-piperidino-butyl-2)-naphthalimide with 200 parts of 30% sodium methoxide solution in 900 parts of methanol at 65° C.

After a reaction period of seven hours, cooling and suction filtration the yield is 140 parts. mp = 182°-184° C.

4.5-dichloro-N(1-piperidino-butyl-2)-naphthalimide is obtained by condensation of 200 parts of 4.5-dichloronaphthalic anhydride with 134 parts of N-2-aminobutylpiperidine in 700 parts of isobutanol at 90° C.

After a reaction period of two hours, cooling and suction filtration, the yield is 278 parts. mp = 142°-144° C.

EXAMPLE 2

43 parts of 4.5-bis-methoxy-ethoxy-N(1-piperidino-butyl-2)-naphthalimide is dissolved in 120 parts of hot acetone, and 18 parts of dimethyl sulfate is dripped in at 56° C. After a reaction period of 2 hours the whole is cooled, suction filtered and washed with acetone. 50 parts of the following compound is obtained which exhibits bluish violet fluorescence in solution in dimethyl formamide

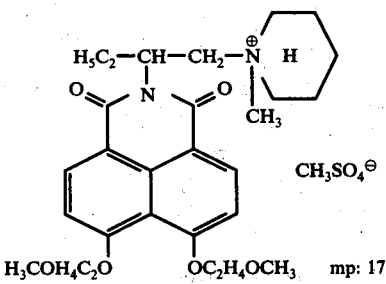

mp: 175-178° C 4.5-bis-methoxy-ethoxy-N(1-piperidino-butyl-2)-naphthalimide is obtained by reaction of 20 parts of 4.5-dichloro-N(1-piperidino-2)-naphthalimide with 19 parts of potassium tert-butoxide in methoxy-ethanol at 80° C. After a reaction period of two hours, cooling and suction filtration the yield is 22 parts. mp = 153°-155° C.

EXAMPLE 3

10 parts of 4.5-dimethoxy-N(1-piperidino-butyl-2)-naphthalimide is dissolved in 90 parts of hot toluene.

15.4 parts of diethyl sulfate is dripped in at 90° to 95° C. After a reaction period of ten hours the whole is cooled, suction filtered and washed with acetone.

12 parts of the following compound is obtained which exhibits violet fluorescence in solution in dimethyl formamide

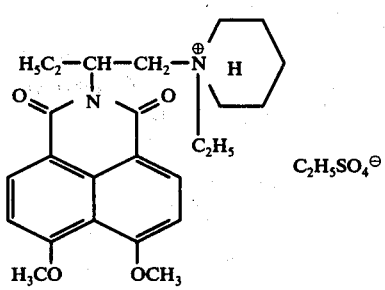

mp = 227-228° C.

EXAMPLE 4

90 parts of 4.5-diethoxy-N(1-piperidino-butyl-2)-naphthalimide is dissolved in 280 parts of hot acetone. 32 parts of dimethyl sulfate is dripped in at 56° C. After a reaction period of 4 hours the whole is cooled, suction filtered and washed with acetone. 114 parts of the following compound is obtained which exhibits violet fluorescence in solution in dimethyl formamide

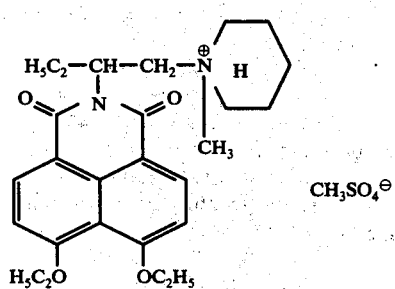

mp = 215-217° C.

EXAMPLE 5

30 parts of 4.5-bis-methoxy-ethoxy-N(1-piperidino-propyl-2)-naphthalimide is dissolved in 85 parts of acetone. 13 parts of dimethyl sulfate is dripped in at 56° C. After a reaction period of 4 hours the whole is cooled, suction filtered and washed with acetone. 35 parts of the following compound is obtained which exhibits bluish violet fluorescence in solution in dimethyl formamide.

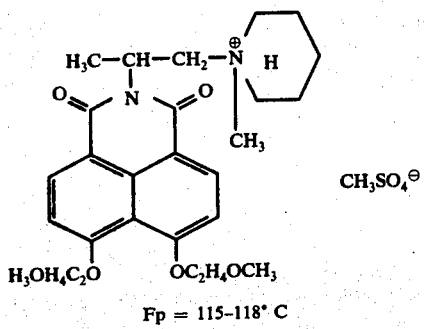

Fp = 115–118° C 4.5-bis-methoxy-ethoxy-N(1-piperidino-propyl-2)-naphthalimide is obtained by reaction of 30 parts of 4.5-dichloro-N(1-piperidinopropyl-2)-naphthalimide with 29 parts of potassium tert-butoxide in 250 parts of methoxy-ethanol at 80° C. After a reaction period of four hours, cooling and suction filtration, the yield is 31 parts. mp = 135°–137° C.

4.5-Dichloro-N(1-piperidinopropyl-2)-naphthalimide is obtained by condensation of 200 parts of 4.5-dichloro-naphthalic anhydride with 132 parts of N-2-aminopropylpiperidine in 700 parts of isobutanol at 90° C. After a reaction period for 8 hours, cooling and suction filtration, the yield is 270 parts. mp = 189°–181° C.

| Example | $R^2$—A | $R^1$ | Fluorescence |
|---|---|---|---|
| 6 | $H_5C_2$—CH—CH$_2$—$\overset{\oplus}{N}$(piperidine with H) $Cl^\ominus$ | $CH_3$ | violet |
| 7 | $H_5C_2$—CH—CH$_2$—$\overset{\oplus}{N}$(pyrrolidine with CH$_3$) $CH_3SO_4^\ominus$ | $CH_3$ | violet |
| 8 | $H_5C_2$—CH—CH$_2$—$\overset{\oplus}{N}$(azepane with CH$_3$) $CH_3SO_4^\ominus$ | $CH_3$ | violet |
| 9 | $H_5C_2$—CH—CH$_2$—$\overset{\oplus}{N}(C_4H_9)_2$ / CH$_3$  $CH_3SO_4^\ominus$ | $CH_3$ | violet |
| 10 | $H_5C_2$—CH—CH$_2$—$\overset{\oplus}{N}(C_2H_5)$ / CH$_3$  $CH_3SO_4^\ominus$ | $CH_3$ | violet |
| 11 | $H_3C$—CH—CH$_2$—$\overset{\oplus}{N}(C_4H_9)_2$ / CH$_3$  $CH_3SO_4$ | $CH_3$ | violet |
| 12 | $H_5C_2$—CH—CH$_2$—$\overset{\oplus}{N}$(piperidine with H, CH$_2$—CH=CH$_2$) $Br^\ominus$ | $C_2H_5$ | bluish violet |
| 13 | $H_5C_2$—CH—CH$_2$—$\overset{\oplus}{N}$(piperidine with H, CH$_2$—C$_6$H$_5$) $Br^\ominus$ | $CH_3$ | violet |
| 14 | $H_5C_2$—CH—CH$_2$—$\overset{\oplus}{N}(CH_3)_3$  $CH_3SO_4^\ominus$ | $CH_3$ | violet |

-continued

| Example | R²—A | R¹ | Fluorescence |
|---|---|---|---|
| 15 | H₇C₃—CH(—)—CH₂—N⁺(piperidine, N-CH₃) H   CH₃SO₄⁻ | CH₃ | violet |
| 16 | H₇C₃—CH(—)—CH₂—N⁺(piperidine, N-CH₃) H   CH₃SO₄⁻ | C₂H₄OCH₃ | bluish violet |
| 17 | H₉C₄—CH(—)—CH₂—N⁺(piperidine, N-CH₃) H   CH₃SO₄ | CH₃ | violet |
| 18 | H₉C₄—CH(—)—CH₂—N⁺(C₄H₉)₂ CH₃   CH₃SO₄ | CH₃ | violet |
| 19 | H₉C₄—CH(—)—CH₂—N⁺(azocane, N-CH₃) H   CH₃SO₄⁻ | CH₃ | violet |
| 20 | —CH₂—C(CH₃)₂—CH₂—N⁺(piperidine, N-CH₃) H   CH₃SO₄⁻ | CH₃ | violet |
| 21 | —CH₂—C(CH₃)₂—CH₂—N⁺(C₂H₅)₂ CH₃   CH₃SO₄⁻ | CH₃ | violet |
| 22 | H₉C₄—CH(—)—CH₂—N⁺(piperidine, N-CH₂—CH=CH₂) H   Br⁻ | CH₃ | violet |
| 23 | H₅C₂—CH(—)—CH₂—N⁺(piperidine, N-C₄H₉) H   Br⁻ | C₂H₅ | bluish violet |
| 24 | H₇C₃—CH(—)—CH₂—N⁺(piperidine, N-C₂H₅) H   C₂H₅SO₄⁻ | CH₃ | violet |

| Example | R²—A | R¹ | Fluorescence |
|---|---|---|---|
| 25 | H₅C₂—CH—CH₂—N⁺(piperidine, C₂H₅)  C₂H₅SO₄⁻  with C₂H₅ | C₂H₄OCH₃ | bluish violet |
| 26 | H₉C₄—CH—CH₂—N⁺(piperidine, C₂H₅)  C₂H₅SO₄⁻ | C₂H₄OCH₃ | bluish violet |
| 27 | H₅C₂—CH—CH₂—N⁺(morpholine, CH₃)  CH₃SO₄⁻ | CH₃ | violet |
| 28 | H₅C₂—CH—CH₂—N⁺(H)(azocane)  CH₃COO⁻ | CH₃ | violet |
| 29 | H₉C₄—CH—CH₂—N⁺(H)(azocane)  HCOO⁻ | CH₃ | violet |

We claim:
1. A naphthalimide compound of the formula

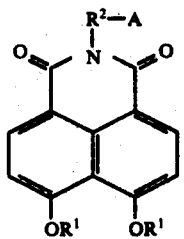

in which
R¹ is C₁- to C₄-alkyl or C₁- to C₄-alkoxyethyl,
R² is branched C₃- to C₆-alkylene,
A is $$-\overset{R^3}{\underset{R}{\overset{|}{N^{\oplus}}}}-R^3 \quad X^{\ominus}$$

R is hydrogen, C₁- to C₄-alkyl, allyl or benzyl, $$N-R^3 \text{ is } N(CH_3)_2, N(C_2H_5)_2, N(C_3H_7)_2, N(C_4H_9)_2,$$
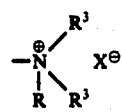

-continued

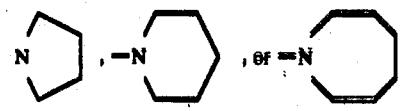

and
X⁻ is an unreactive and colorless anion.
2. A compound according to the formula in claim 1 wherein R¹ is C₁ to C₄-alkyl or CH₃OC₂H₄.
3. A compound according to the formula in claim 1 wherein R¹ is methyl, ethyl or CH₃OC₂H₄.
4. A compound according to the formula in claim 1 wherein R² is

5. A compound according to the formula in claim 1 wherein A is

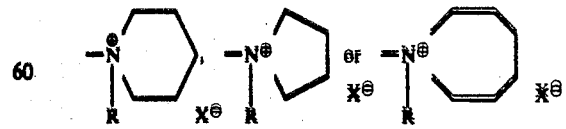

6. A compound according to the formula in claim 1 wherein A is

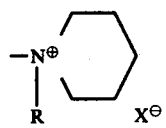

7. A compound according to the formula in claim 1 wherein R is methyl or ethyl.

8. A compound according to claim 1 of the formula

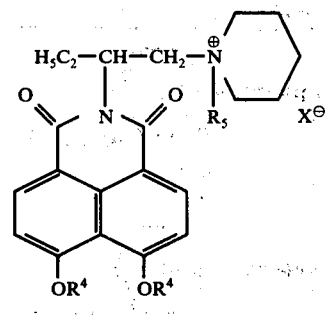

in which
R$^4$ is methyl, ethyl or CH$_3$OC$_2$H$_4$ and
R$^5$ is methyl or ethyl.

9. A compound according to the formula of claim 1 wherein the anion X$^-$ is selected from the group consisting of perchlorate, chloride, bromide, sulfate, hydrogen sulfate, methyl sulfate, ethyl sulfate, acetate, formate, benzenesulfonate, toluenesulfonate, chlorozincate and tetrafluoborate.

* * * * *